US012678087B2

(12) United States Patent
Cuervo et al.

(10) Patent No.: US 12,678,087 B2
(45) Date of Patent: Jul. 14, 2026

(54) IDENTIFICATION OF STABLE ELECTROPHYSIOLOGICAL REGIONS

(71) Applicant: MEDTRONIC, INC., Minneapolis, MN (US)

(72) Inventors: David Calvo Cuervo, Madrid (ES); Omer Berenfeld, Ann Arbor, MI (US)

(73) Assignee: MEDTRONIC, INC., Minneapolis, MN (US)

( * ) Notice: Subject to any disclaimer, the term of this patent is extended or adjusted under 35 U.S.C. 154(b) by 309 days.

(21) Appl. No.: 18/493,079

(22) Filed: Oct. 24, 2023

(65) Prior Publication Data

US 2024/0148311 A1 May 9, 2024

Related U.S. Application Data

(60) Provisional application No. 63/422,563, filed on Nov. 4, 2022.

(51) Int. Cl.
*A61B 5/367* (2021.01)
*A61B 5/00* (2006.01)
*A61B 5/36* (2021.01)

(52) U.S. Cl.
CPC ............... *A61B 5/367* (2021.01); *A61B 5/36* (2021.01); *A61B 5/4836* (2013.01)

(58) Field of Classification Search
None
See application file for complete search history.

(56) References Cited

U.S. PATENT DOCUMENTS

| | | | | |
|---|---|---|---|---|
| 2009/0112109 A1* | 4/2009 | Kuklik | ................. | A61B 5/0536 |
| | | | | 600/509 |
| 2014/0241988 A1* | 8/2014 | Jalife | ................... | A61K 31/713 |
| | | | | 424/9.2 |
| 2014/0323848 A1* | 10/2014 | He | ......................... | A61B 5/361 |
| | | | | 600/509 |

* cited by examiner

*Primary Examiner* — Ankit D Tejani
(74) *Attorney, Agent, or Firm* — Tarolli, Sundheim, Covell & Tummino LLP

(57) ABSTRACT

An example method includes storing reconstructed electrophysiological data sets for at least two baseline time intervals and at least one modulation time interval. The electrophysiological data sets are representative of electrophysiological signals reconstructed at locations across a respective surface of interest within a patient's body based on non-invasively measured electrophysiological signals for respective time intervals. The modulation time interval can overlap with modulating an arrhythmia or arrhythmogenic activity. The method can also include computing dominant frequency maps from the electrophysiological signals reconstructed for at least two baseline data sets and the at least one modulation data set. The method can also include analyzing the dominant frequency maps to determine an indication of dominant frequency stability across at least a portion of the surface of interest.

25 Claims, 9 Drawing Sheets

100

ACQUIRE BASELINE EGM DATA SETS — 102

MODULATE CARDIAC PHYSIOLOGY (E.G., ADENOSINE INFUSION) — 104

ACQUIRE EGM DATA SET FOR MODULATED PHYSIOLOGY — 106

RECONSTRUCT EP SIGNALS — 108

IDENTIFY SEGMENTS OF INTEREST — 110

COMPUTE DOMINANT FREQUENCY MAPS FOR EACH DATA SET — 112

DETERMINE BASAL STABILITY — 114

DETERMINE DF STABILITY INDEX (DFSI) — 116

GENERATE DFSI MAP — 118

300

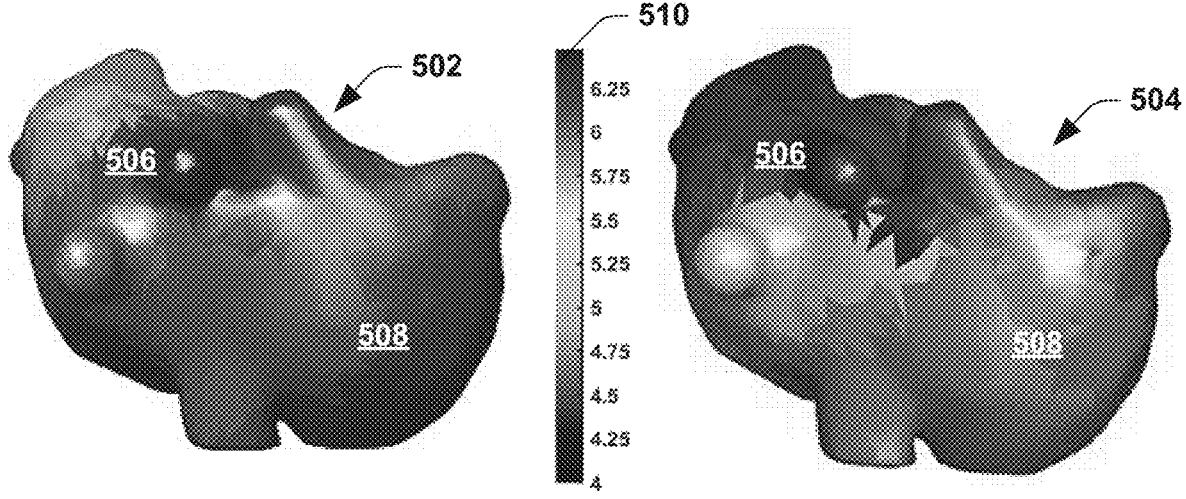
FIG. 5A                          FIG. 5B
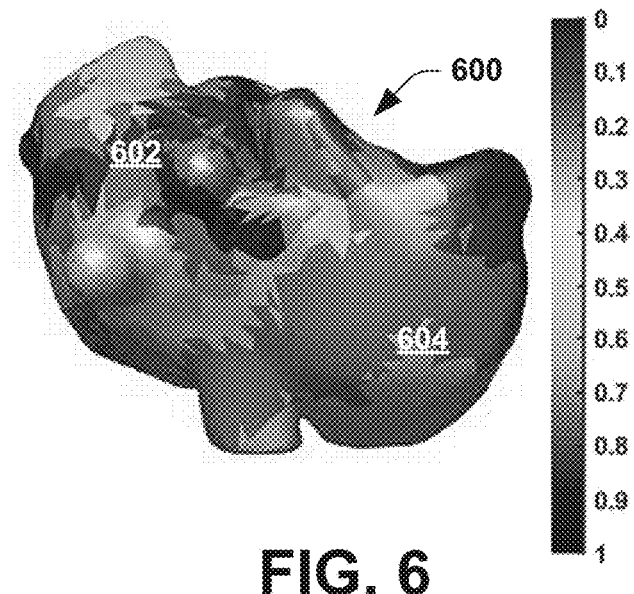
FIG. 6

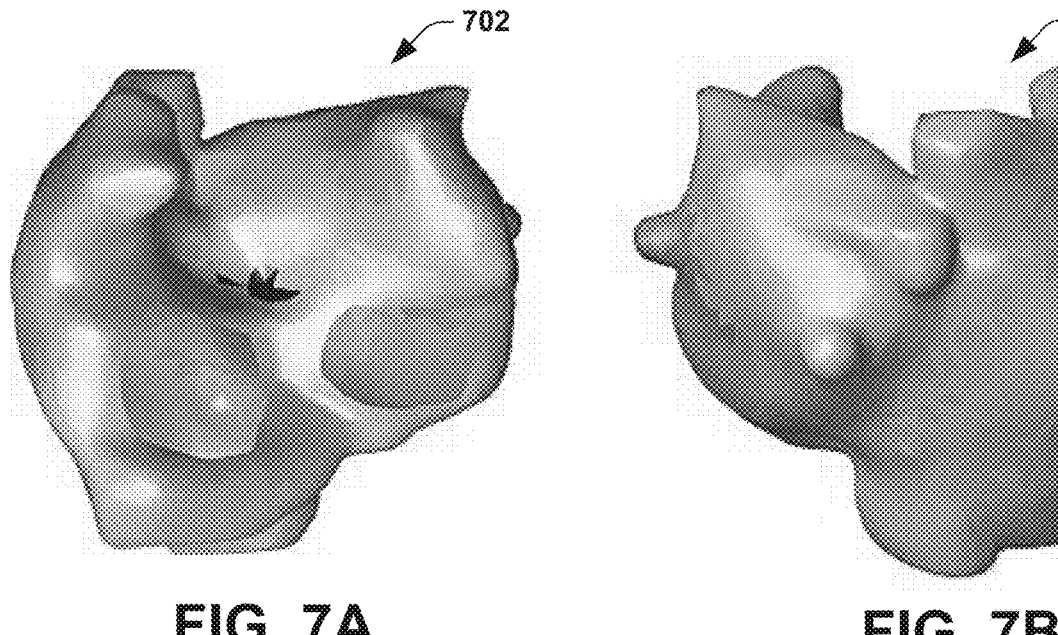
FIG. 7A                                    FIG. 7B
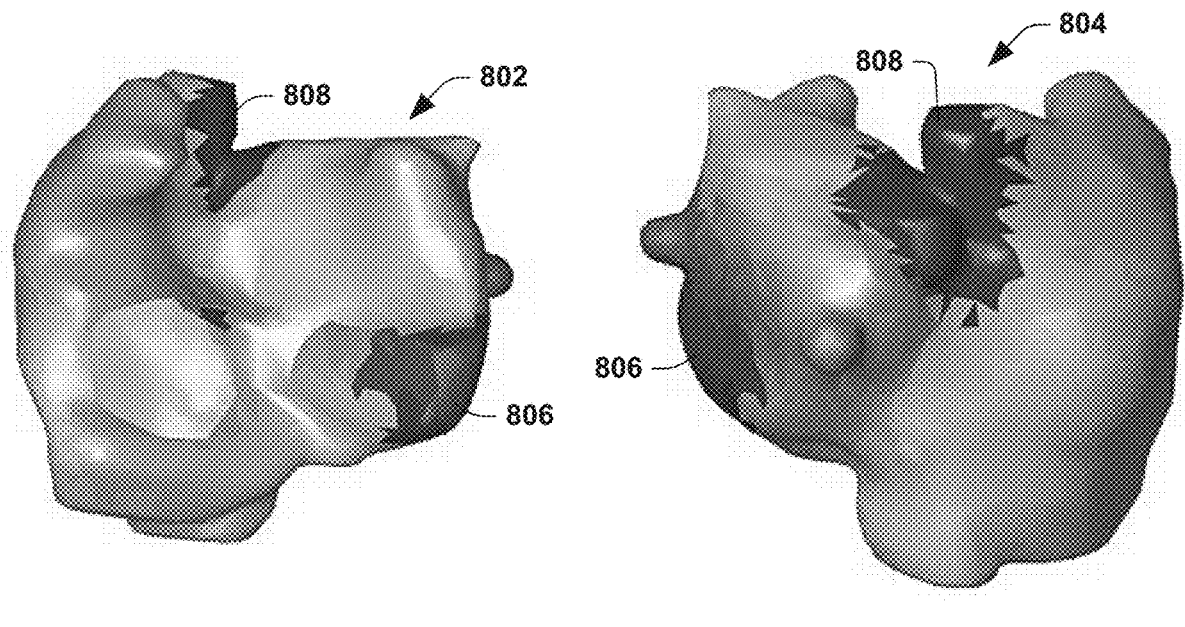
FIG. 8A                                    FIG. 8B

902

904

IDENTIFICATION OF STABLE ELECTROPHYSIOLOGICAL REGIONS

CROSS-REFERENCE TO RELATED APPLICATION

This application claims priority to U.S. Provisional Patent Application No. 63/422,563, which was filed 4 Nov. 2022, which is incorporated herein by references in its entirety.

FIELD

The present technology is generally related to identifying ablation targets.

BACKGROUND

Cardiac ablation is used to remove or terminate an electrical pathway from sections of the heart to reduce or prevent the occurrence of some cardiac arrhythmias, such as atrial fibrillation (AF), atrial flutter and Wolff-Parkinson-White syndrome, as well as other dysfunctions. The mechanisms underlying AF, the most common arrhythmia in the population, are still not fully clear and its therapy can be suboptimal. Ablation to isolate the pulmonary veins (PVs) has become a common practice for paroxysmal AF. However, it can be more challenging to identify appropriate targets to improve outcomes for patients with persistent AF.

SUMMARY

The techniques of this disclosure generally relate to identifying ablation targets and providing guidance.

In one aspect, the present disclosure provides a method that includes storing, in one or more non-transitory machine-readable media, electrophysiological data sets for multiple time intervals. At least one modulation data set includes electrophysiological signals measured concurrently with modulating behavior of an arrhythmia or arrhythmogenic activity. The method also includes reconstructing, by a processor, electrophysiological signals at locations across a surface of interest based on at least some of the electrophysiological data sets and geometry data. The geometry data can be representative of geometry of the surface of interest and geometry of locations where the electrophysiological signals were measured. The method also includes computing, by the processor, dominant frequency maps from the electrophysiological signals reconstructed for at least two baseline data sets and at least one modulation data set. The method also includes analyzing, by the processor, the dominant frequency maps to determine an indication of dominant frequency stability across at least a portion of the surface of interest.

In another aspect, the disclosure provides a computer implemented method that includes storing reconstructed electrophysiological data sets for at least two baseline time intervals and at least one modulation time interval. The electrophysiological data sets are representative of electrophysiological signals reconstructed at locations across a respective surface of interest within a patient's body based on non-invasively measured electrophysiological signals for respective time intervals. The modulation time interval can overlap with modulating an arrhythmia or arrhythmogenic activity. The method can also include computing dominant frequency maps from the electrophysiological signals reconstructed for at least two baseline data sets and the at least one modulation data set. The method can also include analyzing the dominant frequency maps to determine an indication of dominant frequency stability across at least a portion of the surface of interest.

In another aspect, the disclosure provides a system that includes a computing apparatus having non-transitory memory to store data and instructions executable by a processor thereof. The data can include reconstructed electrophysiological data sets for at least two baseline time intervals and at least one modulation time interval. The reconstructed electrophysiological data sets are representative of electrophysiological signals reconstructed at locations across a respective surface of interest based on non-invasive electrophysiological measured for respective time intervals. The at least one modulation time interval can coincide with modulating an arrhythmia or arrhythmogenic activity. The instructions can be programmed to compute dominant frequency maps from the reconstructed electrophysiological data sets for the at least two baseline time intervals and the at least one modulation time interval. The instructions can also be programmed to analyze the dominant frequency maps and determine an indication of dominant frequency stability across at least a portion of the surface of interest.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIGS. 5A and 5B are dominant frequency maps that illustrate examples of dominant frequency determined for respective baseline data sets.

FIG. 6 is a graphical map that illustrates an example of baseline stability.

FIGS. 7A and 7B are graphical maps that illustrate an example of dominant frequency computed for a baseline data set.

FIGS. 8A and 8B are graphical maps that illustrate an example of dominant frequency for a modulation data set.

DETAILED DESCRIPTION

This disclosure relates to systems and methods to determine stable electrophysiological regions. Systems and methods described herein can utilize non-invasive panoramic mapping to provide an atria-wide (or greater) characterization of the combined impact of adenosine on both reentrant activity and local activation rate. For example, the systems and methods implement non-invasive panoramic mapping with dominant frequency comparative analysis with an adenosine challenge to characterize dominant frequency stability, which is used to identify treatment targets, such as ablation targets. As described herein, the systems and methods described herein can help improve ablation outcomes for patients, including persistent AF patients.

Figure 1:
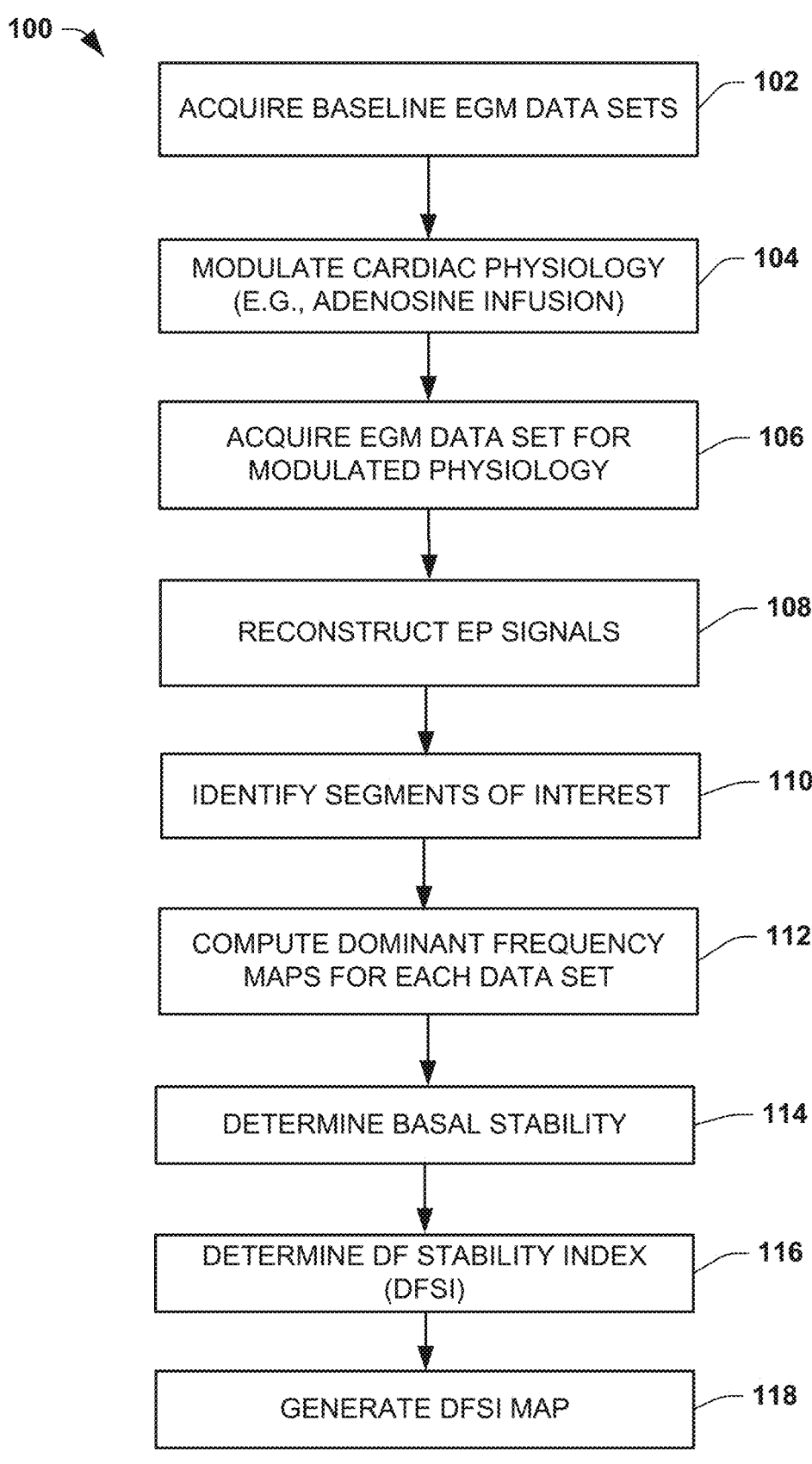
FIG. 1 is a flow diagram that illustrates an example method to identify ablation targets.

FIG. 1 is a flow diagram that illustrates an example method 100 that can be used to provide guidance. In an example, the method 100 is used to identify treatment targets (e.g., ablation targets) for physicians to treat patients, particularly persistent AF patients. The guidance can include providing a graphical visualization, such as a panoramic graphical map of the heart representative of dominant frequency stability across the heart, as determined by the method 100.

The example method 100 begins at 102 in which baseline (also referred to as basal) electrophysiological signal data sets are acquired. The baseline data sets can be acquired prior to treatment or administration of a modulating agent or after the effects of such agent have sufficiently diminished. For example, two or more baseline data sets can be acquired by an arrangement of body surface sensors distributed across a patient's body, which are configured to measure electrophysiological signals (e.g., electrograms (EGM)) from the body surface non-invasively. As examples, the sensors can be in the form of one or more patches or a vest having a set of electrodes in fixed arrangement or individual electrodes configured to be attached to the patient's thorax. The number and distribution of sensors can vary according to application requirements and/or a given use environment.

The electrodes can acquire cardiac electrophysiological signals including signal content representative of electrophysiological signals from more than one chamber of the heart, such as both atria or up to including the entire heart. The respective data sets thus represent baseline electrophysiological activity over respective different time intervals. The time intervals for the respective baseline data set can span the same length of time or different periods of time. The time intervals can be selected (e.g., by signal acquisition function of a mapping system) automatically or in response to a user input. The data sets acquired at 102 can be stored in memory (e.g., one or more non-transitory machine-readable media) as described herein.

At 104, the method includes modulating behavior of an arrhythmia or arrhythmogenic activity. For example, a concentration of adenosine or other bioequivalent modulating agent is administered to the subject. Other modulating agents (e.g., chemical and/or electrical agents) can be used in other examples. The modulating agent can be adapted, as administered, to modulate reentrant activity, accelerate the dominant frequency of reentrant activity, and/or accelerate local activation rate in a predictable manner. For example, in comparison with baseline data sets cycle length of rotational domains may shorten and/or partial atrial acceleration may occur at localized spatial regions responsive to the modulation at 104.

At 106, a modulation data set of electrophysiological signals is acquired. The modulation data set can include electrophysiological signals measured concurrently with modulating (or inducing a change in) behavior or properties of an arrhythmia or arrhythmogenic activity. The data set of electrophysiological signals representative of signals measured during modulation of the arrhythmia or arrhythmogenic activity can include data acquired for one or more time intervals during such modulation. In an example, the modulation data set includes one or more time intervals during a peak effect of the modulating agent (e.g., peak adenosine effect). The peak effect can be indicated by one or more prolonged RR intervals. The prolonged RR intervals can be detected by manual observation of EGMs or by an automatic RR detection algorithm, and used to identify the time interval (e.g., start and stop times) for the modulation data set. The data set(s) acquired at 106 can be stored in memory.

At 108, the method includes reconstructing electrophysiological signals at locations across a surface of interest based on at least some of the electrophysiological data sets and geometry data. For example, a processor is programmed to reconstruct electrophysiological signals onto locations (e.g., nodes) across a surface of interest based on at least some of the electrophysiological data sets and geometry data. The processor can be programmed to reconstruct the electrophysiological signals for at least two of the baseline and one or more modulation data sets. The reconstruction can be implemented by solving the inverse problem, such as described herein with respect to FIG. 3. As described herein, the surface of interest can include more than one chamber of the heart, such as both atria or the whole heart, and the reconstructed electrophysiological signals can represent the electrical activity at respective locations on such surface for each of the respective baseline and modulation data sets.

The geometry data is representative of spatial geometry of the surface of interest on which the electrophysiological signals are reconstructed at 108. The geometry data also is representative of the geometry of locations (e.g., body surface sensor locations) where the electrophysiological signals were measured. The geometry data can describe the surface of interest and sensor locations as including respective spatial coordinates in one or more respective three-dimensional spatial domains. If the data is generated in different spatial domains, the respective geometries can be co-registered into a common spatial coordinate system. The reconstructed electrophysiological data for the baseline and modulation data sets can be stored in memory for further processing, as described herein.

At 110, segments of interest are identified for each of the data sets. The segments can be identified in the respective data sets by specifying start and stop times for segments that are substantially free of ventricular depolarization. For example, the segments are TQ segments of the electrocardiogram (ECG) cardiac cycles recorded in the respective data sets. The segments can be identified manually in response to a user input specifying start and stop types of the respective segments or automatic signal processing can be used to identify such segments. The segment identification can be implemented on the electrophysiological signals acquired at 102 and 106 or on the signals that have been reconstructed at 108. For example, the identified start and stop times for the identified segments can be stored in memory (e.g., as tags or metadata) associated with the reconstructed signal data provided for each of the baseline and modulation data sets.

Figure 2:
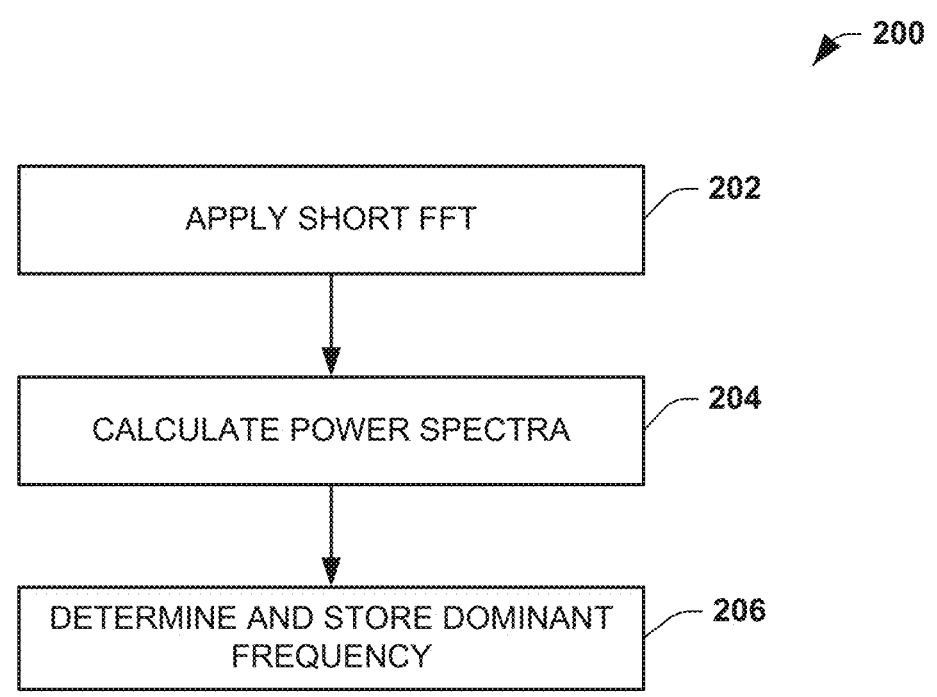
FIG. 2 is a flow diagram that illustrates an example method to generate a dominant frequency map.

At 112, dominant frequency maps are computed based on the reconstructed signal data. For example, a processor is programmed to compute dominant frequency maps based on the electrophysiological data representing reconstructed electrophysiological signals for at least two baseline data sets and the modulation data set. In an example, the dominant frequency maps are computed for the segments of the electrophysiological signals identified at 110 selected from the baseline and modulation data sets. One example of a method that can be used to compute the dominant frequency maps is shown in FIG. 2. Other approaches can also be used to determine the dominant frequency maps at 112.

At 114, baseline stability is determined based on the dominant frequency maps generated (at 112) for the baseline data sets. For example, a processor is programmed to determine baseline stability by computing a difference between at least first and second baseline dominant frequency (DF) maps (i.e., $\Delta DF=DF\_Basal1-DF\_Basal2$). The difference can be computed between dominant frequency values at respective locations (nodes) across the surface of interest of the baseline dominant frequency maps. The absolute difference can be normalized and can be subtracted from unity value (e.g., 1) (e.g., normalized baseline stability=$1-|\Delta DF|_{normalized}$).

At 116, a dominant frequency stability index (DFSI) is determined based on the dominant frequency map for the modulated data set and the baseline stability determined at 114. For example, the baseline stability map, which is representative of normalized dominant frequency stability across the surface interest, is applied to weight the dominant frequency map for the modulation data set. At 118, a corresponding DFSI map can be generated to represent the DFSI at respective locations across the surface of interest. By applying the weighting to the dominant frequency map for the modulated data set, the resulting DFSI map can localize regions having the highest DF acceleration relative to baseline stability.

For example, the DFSI map can be rendered on a display device as a panoramic graphical representation of the DFSI map in which the DFSI values are represented using a color or other scale to describe the adjusted dominant frequency stability across the surface of interest. The graphical representation of the DFSI map can be visualized on a display to show electrophysiological signals across a surface of interest (e.g., a cardiac surface or envelope). The surface of interest can be an epicardial surface, an endocardial surface or a virtual envelope, and include more than heart chamber, such as both atria or up to including the entire heart. The graphical DFSI map can be used to identify targets (e.g., ablation targets) on the surface of interest, individually or in conjunction with other forms of guidance.

As an example, the processor can be programmed to provide one or more other forms of guidance, such as by generating a rotor map for the surface of interest, which localizes one or more rotational domains (e.g., stable rotational domains). The processor can be further programmed to co-localize the rotor map with the DFSI map and provide a resulting composite map by combining the rotor map and the DFSI map. The composite map thus can identify a subset of targets for treatment based on a correlation between the respective maps.

In an example, a processor is programmed to compute the phase over one or more time intervals for a multitude of points based on the reconstructed electrophysiological signals. The computed phase can be utilized to identify and characterize fibrillation mechanisms including but not limited to focal points, triggered activity, micro and macro-reentrant circuits and localized rotational domains in a patient's heart. The characterizations can be in the form of one or more graphical anatomical maps, including dynamic animated movies depicting rotors and associated movement as well as other characterizations of temporally and spatially consistent (e.g., panoramic visualization) as clinical targets. For example, U.S. Pat. No. 9,427,166 describes examples of approaches that can be implemented to provide additional guidance, namely to provide maps that identify stable rotational domains, which can be combined with the dominant frequency maps, including the DFSI map, to identify spatially one or more targets for treatment. U.S. Pat. No. 10,959,638 describes other examples of mapping of conduction velocity or other propagation patterns that can be used to provide guidance that also can be combined with the dominant frequency maps, including the DFSI map, to identify spatially one or more targets for treatment. U.S. Patent Publication No. 2016/0338772 and U.S. Pat. No. 10,959,638 are included as appendices and incorporated herein by reference. Other forms of guidance can also be combined with the approach described herein to identify targets for treatment.

In some examples, a physician can locate a target site on a cardiac surface (endocardial and/or epicardial), as identified by the guidance provided in the DFSI map, individually or in combination with other guidance, and perform a desired intervention at the target site, such as an ablation. For example, ablation therapy is implemented at the one or more identified targets, such as using radiofrequency ablation, radiation ablation, cryoablation, noninvasive cardiac radioablation, or pulsed-field ablation. After performing the ablation, the patient's cardiac electrophysiology can be re-evaluated, such as using the method 100 and/or other diagnostic methods, to determine whether the treatment has reduced or eliminated the region or regions of dominant frequency stability.

While the method 100 is described as including acquisition of the data sets serially and in real time, the respective data sets can be acquired before or during any analysis thereof and in different orders from that shown in FIG. 1. That is, the analysis and processing, including any combination or subset of 108-118, can be performed in real time during a procedure or before or after a procedure, such as for pre-procedure planning or post-procedure evaluation. Additionally or alternatively, the analysis and processing, including any combination or subset of 108-118, can be performed locally, remotely or both locally and remotely.

FIG. 2 illustrates an example method 200 to compute dominant frequency maps, such as for the respective baseline and modulation data sets. The method is one example approach to determine dominant frequency, which can be used at 112 in the method of FIG. 1. An instance of the instructions programmed to implement the method 200 can be applied to determine respective dominant frequency maps for each of the baseline and modulation data sets, which can be computed in a parallel or serial manner.

The method 200 begins at 202 in which a short-time Fourier transform is applied to respective signals in a given data set to produce a respective frequency domain representation of such data set for identified segments of the reconstructed electrophysiological signals, including at least two baseline data sets and the modulated data set(s). As described herein, the segments can be identified as segments of the cardiac cycle substantially free of ventricular depolarization. For example, the segments to which the short-time Fourier transform is applied are TQ segments to determine frequency and phase content of respective segments as they change over time. Other transforms or frequency analysis methods can be used in other examples.

At 204, power spectra are computed for the baseline and modulation frequency domain data sets. In an example, a processor is programmed to compute the power spectra using the Welch's averaging approach of the power spectra.

At 206, the dominant frequency for each location in the respective data set is determined by identifying the frequency with highest power in the power spectra determined at 204 (e.g., in the Welch's averaged power spectra) at a resolution of about 0.112 Hz (Supplemental Material Figures S2). The dominant frequencies derived at 206 for the respective locations across the surface of interest for a respective data set can be stored in memory to provide a resulting dominant frequency map for the data set.

Figure 3:
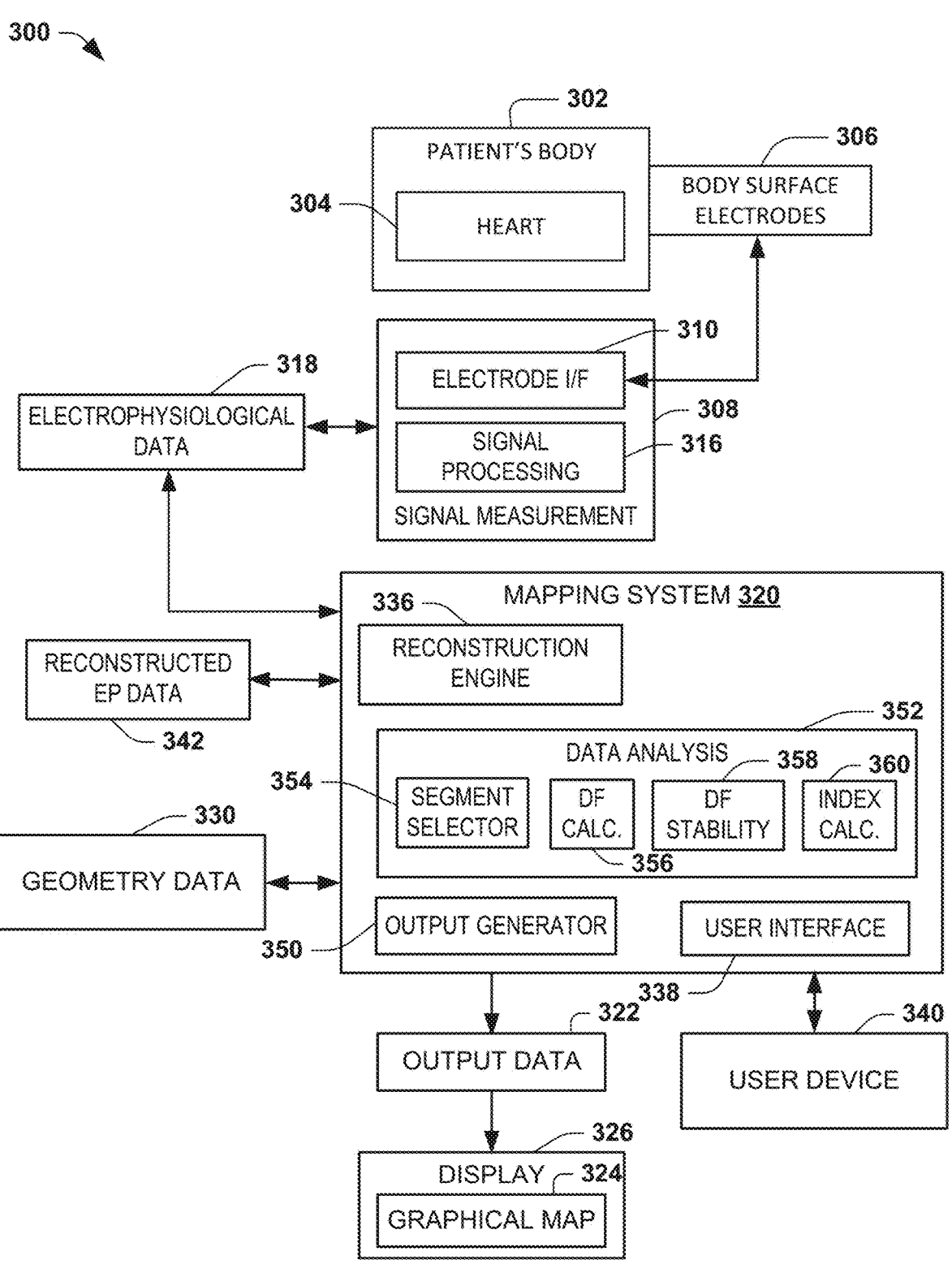
FIG. 3 is a block diagram of an example system that includes a mapping system configured to identify ablation targets.

FIG. 3 depicts an example of a system 300 for monitoring and mapping electrophysiological measurements from a patient's body 302, namely electrophysiological activity emanating from the patient's heart 304. The system 300 can be used to implement the methods 100 and 200 of FIGS. 1 and 2, including any one or more portions thereof up to and including the entirety of one or both such methods.

The system 300 includes an arrangement of body surface electrodes 306, which are coupled to a signal measurement system 308. For example, each of the electrodes 306 is coupled to the signal measurement system 308 through a respective electrically conductive channel (e.g., including electrically insulated wires and/or traces) to communicate electrophysiological signals measured non-invasively from an outer surface of the patient's body. The electrically conductive channels for the electrodes 306 can include an arrangement of connectors configured to couple to respective connectors (e.g., male and female connectors) of an electrode interface 310 of the measurement system 308. In other examples, the electrodes 306 may be coupled to the electrode interface 310 through other forms of communication (e.g., optical fiber or wireless leads).

The body surface electrodes 306 include an arrangement of multiple electrodes (e.g., 20-300 sensor electrodes or any permutation thereof) distributed across an outer surface of the patient's body 302. In an example, the body surface electrodes 306 are distributed completely around the thorax, such as can be mounted to a wearable garment (e.g., vest) in which each of the electrodes has a known location in a given coordinate system. For example, body surface electrodes 306 can be implemented as a non-invasive type of sensor apparatus as disclosed in U.S. Pat. No. 9,655,561, entitled Multi-Layered Sensor Apparatus, which is incorporated herein by reference. Other configurations and numbers of body surface electrodes 306 could be utilized in other examples, such as on patch electrodes or through individually placed electrodes.

As described above, the electrode interface 310 has respective inputs coupled to each of the electrodes 306. The signal measurement system 308 can also include signal processing circuitry 316 configured to process electrical signals received by the electrodes 306. The signal processing circuitry 316 can be implemented as hardware and/or software, such as including a digital signal processor and other processing circuitry and machine readable instructions (executable by a processor) configured to remove noise (e.g., line noise) and convert the received signals into a desired format for storing the measured electrophysiological signals as electrophysiological data 318. The measured electrophysiological data 318 thus can include unipolar, bipolar or a combination of unipolar and bipolar electrophysiological signals depending on the configuration of electrodes 306 and processing of the measured signals. The signal processing circuitry 316 can also add channel information (e.g., to specify electrode number or location), add timestamps (e.g., to specify the time or each measurement sample) or perform other signal processing functions that may be desired. The electrophysiological data 318 thus can include signal measurement values for each sample as well as additional information, such as timestamps and channel information.

The system 300 also includes a mapping system 320 configured to generate output data 322, which may be used to render a graphical map (e.g., a map on a heart model) 324 and/or display processed electrical signals on a display 326. The mapping system 320 can also provide information in other display formats to provide guidance to a user (e.g., person and/or machine) representative of and/or derived from electrical activity that may be measured by any combination of the electrodes 306. The mapping system 320 can be a computer-implemented apparatus that includes one or more processors and memory (one or more non-transitory computer-readable media) to store data and machine-readable instructions, which are executable by the processor to perform respective functions described herein. In another example, the mapping system 320 can be machine-readable instructions, which are stored in one or more non-transitory media and are executable by the processor to perform respective functions described herein (e.g., computer software code to perform various parts of the methods 100 and 200).

The mapping system 320 is programmed to generate the output data 322 based on the electrophysiological data 318 and geometry data 330. The geometry data 330 can include electrode geometry data and anatomical geometry data. The electrode geometry data can represent spatial locations of respective body surface electrodes 306 in three-dimensional space. The anatomical geometry data represents spatial geometry of the surface of interest of the patient in three-dimensional space.

As an example, the geometry data 330 can be derived from imaging data acquired by a three-dimensional medical imaging modality. In one example, an anatomical model can be constructed based on imaging data obtained (e.g., by a medical imaging modality) for the patient to provide spatial coordinates for points across the patient's heart and, in some cases, in which the electrodes 306 are positioned on the patient's body when the medical image is acquired, for the locations of the body surface electrodes 306 positioned on the outer surface of the patient's body. The medical imaging data can be generated for the patient's body using a medical imaging modality, such as multi-plane x-ray, computed tomography (CT), magnetic resonance imaging (MRI), ultrasound, positron emission tomography (PET), single-photon emission computed tomography (SPECT) and the like. The electrode locations and locations of the surface (or surfaces) of interest can be identified in a respective coordinate system of the acquired images through appropriate image processing, including extraction and segmentation. For instance, segmented image data can be converted into a two-dimensional or three-dimensional graphical representation that includes the volume of interest for the patient. Appropriate anatomical or other landmarks can be identified in the geometry data 330 to facilitate spatial registration of the electrophysiological data 318. The identification of such landmarks can be done manually (e.g., by a person via image editing software) or automatically (e.g., via image processing techniques). In another example, the location of the body surface electrodes 306 can be acquired by a digitizer, manual measurements or another non-imaging based technique (e.g., a navigation system).

The mapping system 320 can include a spatial registration function (e.g., machine-readable instructions) programmed to co-register the electrode geometry data and the anatomical geometry data in a common coordinate system. The spatial registration function can implement one or more transforms to align spatially respective data sets for location of the body surface electrodes 306 and the anatomical geometry for the surface of interest. In an example where the system 300 is used intraprocedurally, such as with a catheter or other invasive device to administer a treatment (e.g., ablation) or invasively acquire electrophysiological measurements, the system 300 can also include a navigation system (not shown, but see e.g., FIG. 4). The navigation system can localize the catheter or other device, and the registration function can further implement co-registration of catheter or other device into a common coordinate system.

The mapping system 320 also includes a reconstruction engine 336 (e.g., instructions) programmed to compute reconstructed electrophysiological signals for locations on the surface of interest within the patient's body 302. For example, the reconstruction engine 336 includes instructions programmed to perform the reconstruction at 108 in the method 100 of FIG. 1. The reconstruction engine 336 can thus compute the reconstructed signals (e.g., electrical potentials) on the surface of interest by executing machine-readable instructions (e.g., an algorithm) to reconstruct electrical signals spatially and temporally on to the surface of interest based on the electrophysiological data 318 and the geometry data 330. For example, the reconstruction engine 336 is configured to compute respective reconstructed electrophysiological signals for a plurality of cardiac nodes spatially distributed over surface of interest based on the electrophysiological data 318 measured non-invasively over one or more time intervals. In some examples, the number of cardiac nodes can be greater than 1,000 or 2,000 or more depending upon a desired resolution and the size of the surface of interest.

The reconstructed electrophysiological signals are generated based on a plurality of electrophysiological signal data sets, including at least two baseline data sets and one or more modulation data sets. As described herein, the modulated data set(s) includes electrophysiological signals measured while modulating properties or behavior of an arrhythmia or arrhythmogenic activity in response to administering a concentration of adenosine or other modulating agent (e.g., chemical and/or electrical agent) to the patient's body 302. The modulating agent can be adapted, as administered, to modulate reentrant activity and/or local activation rate in a desired manner. For example, in comparison with baseline data sets, cycle length of rotational domains may shorten and/or partial atrial acceleration may occur at localized spatial domains responsive to the modulating agent. In an example, the electrophysiological data 318 associated with the baseline and modulation data sets can be tagged (e.g., in response to a user input via user interface 338 or by an automated function), such as to identify time intervals for each respective data set accordingly.

As described herein, the geometry data 330 includes three-dimensional spatial information representing the surface (or surfaces) of interest describing a surface having locations (e.g. nodes) on to which reconstructed signals are computed (by engine 336) co-registered with respective locations where electrophysiological measurements are made (e.g., by the 306). The reconstruction engine 336 can calculate the reconstructed electrical signals on the surface of interest for one or more surfaces of interest over one or more time intervals. The time interval(s) may be selected through a user interface 338 in response to a user input entered by a user device 340 (e.g., mouse, keyboard, touchscreen interface, gesture interface or the like). The reconstructed electrophysiological signals generated can be stored as reconstructed electrophysiological data 342 in memory for each of the respective data sets.

By way of example, the reconstruction engine 336 includes instructions programmed to generate a transfer matrix based on the geometry data 330. As described herein, the geometry data 330 used by the transfer matrix generator 346 includes information describing anatomical geometry of the surface of interest and geometry of the respective electrodes 306, which have been co-registered (e.g., by spatial registration function 332) in a common spatial coordinate system (e.g., with respect to patient anatomy). The anatomical geometry may be implemented as a mathematical model (e.g., a spline or mesh or point cloud) that defines locations (e.g., a point cloud) across the surface of interest. The electrode geometry can also be implemented as a model that defines spatial coordinates of the electrodes in the common coordinate system.

As a further example, the reconstruction engine 336 includes code programmed to solve the inverse problem for computing reconstructed electrical signals on the surface of interest. In an example, the reconstruction engine 336 is programmed to implement MFS electrocardiographic imaging similar to that disclosed in U.S. Pat. No. 7,983,743, which is incorporated herein by reference. Other useful examples of inverse algorithms that can be implemented by the reconstruction engine 336 to reconstruct include the boundary element method (BEM), such as disclosed in U.S. Pat. Nos. 6,772,004, and 9,980,660, each of which is incorporated herein by reference. The reconstruction engine 336 further may employ a regularization technique (e.g., Tikhonov regularization) to estimate values for the reconstructed electrical signals on the surface of interest. The reconstruction engine 336 can implement any of a variety of approaches to solve the inverse problem for reconstructing the electrophysiological signals onto one or more surfaces of interest and provide corresponding reconstructed electrophysiological data 342.

The mapping system 320 also includes an output generator 350 that is programmed to generate an the output data 322, such as corresponding to a map that can be rendered on the display 326 to graphically visualize the reconstructed electrical signals on the surface of interest, such as in response to a user input via a user interface 338. As disclosed herein, the surface of interest may be an epicardial surface, an endocardial surface, or a combination of epicardial and endocardial surfaces. Alternatively, the surface of interest can be a virtual cardiac envelope, such as a surface residing between the center of a patient's heart and the body surface where the electrodes are positioned. The surface of interest may encompass more than one chamber of the heart, such as both atria or up to including the entire cardiac surface, such as described herein. The surface and view thereof can be set in response to a user input via the user interface 338.

In a further example, the output generator 350 is programmed to generate output data 322 based on one or more data analysis functions 352. The data analysis functions 352 can include instructions executable by one or more processors to perform various functions disclosed herein (e.g., computer software code to perform various parts of the methods 100 and 200). In the example of FIG. 1, the data analysis functions include a segment selector 354, a dominant frequency calculator 356, a dominant frequency stability function 358 and a dominant frequency stability index calculator 360. Thus, the data analysis functions 352 can perform calculations and associated functions based on electrophysiological data 318, the reconstructed electrophysiological data 342, geometry data 330, or based on a combination of electrophysiological and spatial information.

The segment selector 354 is programmed to select segments of interest in each of the baseline and modulation data sets, such as by identifying segments that are substantially free of ventricular activity for the time intervals that form the respective data sets (e.g., at least two baseline and one or more modulation data sets). For example, the segment selector 354 includes computer software code programmed to perform the identification at 110 of FIG. 1. The segments can be selected manually in response to a user input to the user interface 338, such as through the user device 340. Alternatively, the segments can be selected automatically. For example, the segment selector 354 is programmed to identify TQ segments by specifying start and stop time values for respective TQ segments. The segment selector 354 can identify the respective time intervals from the electrophysiological data 318 (e.g., body surface signals), from the reconstructed electrophysiological data 342 (e.g., reconstructed signals) or from a combination of body surface and reconstructed signals. The body surface signals can be measured using the same electrodes or a subset thereof used to make the body surface measurements to provide the electrophysiological data 318, or a separate set of electrodes can be used in addition to the set of body surface electrodes. The identified segments in each of the baseline and modulation data sets can be stored in memory.

The dominant frequency calculator 356 is programmed to compute dominant frequency maps based on the reconstructed signal data for at least two baseline data sets and the modulation data set. For example, the dominant frequency calculator 356 includes computer software code programmed to perform the computations at 112 of FIG. 1. As another example, the dominant frequency calculator 356 includes computer software code programmed to perform the method 200 of FIG. 2. Thus, the dominant frequency calculator 356 can compute dominant frequency maps for the identified segments (e.g., identified by the segment selector 354) in the respective baseline and modulation data sets based on the reconstructed electrophysiological data 342 of the electrophysiological signals. The resulting dominant frequency maps for each respective data set thus provides an indication of dominant frequency at respective locations (e.g., nodes) across the surface of interest, which can be stored in memory. In some examples, such as in response to a user input through the user interface 338, the output generator 350 can produce output data 322 that includes a graphical map for one or more of the dominant frequency maps determined by the dominant frequency calculator 356.

The dominant frequency stability function 358 is programmed to determine an indication of dominant frequency stability across the surface of interest, such as based on the baseline dominant frequency maps determined by the dominant frequency calculator 356. For example, the dominant frequency stability function 358 includes computer software code programmed to perform the determinations at 114 of FIG. 1. The dominant frequency stability function 358 can be programmed to determine baseline stability by computing a difference between respective baseline dominant frequency maps (e.g., $\Delta DF = DF\_Basal1 - DF\_Basal2$). The difference can be computed between dominant frequency values at respective locations (nodes) across the surface of interest of the baseline dominant frequency maps. A stability measure can be calculated, for example, by subtracting the normalized absolute difference from a unity value (i.e., 1) and taking the absolute value of such value (e.g., normalized baseline stability$=1-|\Delta DF|_{normalized}$, where the value 1 corresponds to maximal stability). In some examples, such as in response to a user input through the user interface 338, the output generator 350 can produce output data 322 that includes a graphical map for the baseline stability map determined by the function 358.

The index calculator 360 is programmed to compute an indication of an adjusted index of dominant frequency stability based on the dominant frequency map for the modulated data set and the baseline stability determined at 114. For example, the index calculator 358 includes computer software code programmed to perform the determination at 116 in FIG. 1. The index calculator 360 can be programmed to compute an index value, which represents DFSI at respective locations across the surface of interest, by weighting values of the dominant frequency map for the modulation data set with respective values of the dominant frequency stability map. The resulting DFSI map can specify regions having highest DF acceleration relative to baseline.

In some examples, such as automatically or in response to a user input through the user interface 338, the output generator 350 can produce output data 322 that includes a graphical representation of the DFSI map. For example, the display 326 renders the DFSI map as a panoramic graphical representation in which the DFSI values are represented using a color or other scale to describe the adjusted dominant frequency stability across the surface of interest. The graphical DFSI map can be used to identify targets (e.g., ablation targets) on the surface of interest, individually or in conjunction with other forms of guidance, such as shown in FIG. 4.

Figure 4:
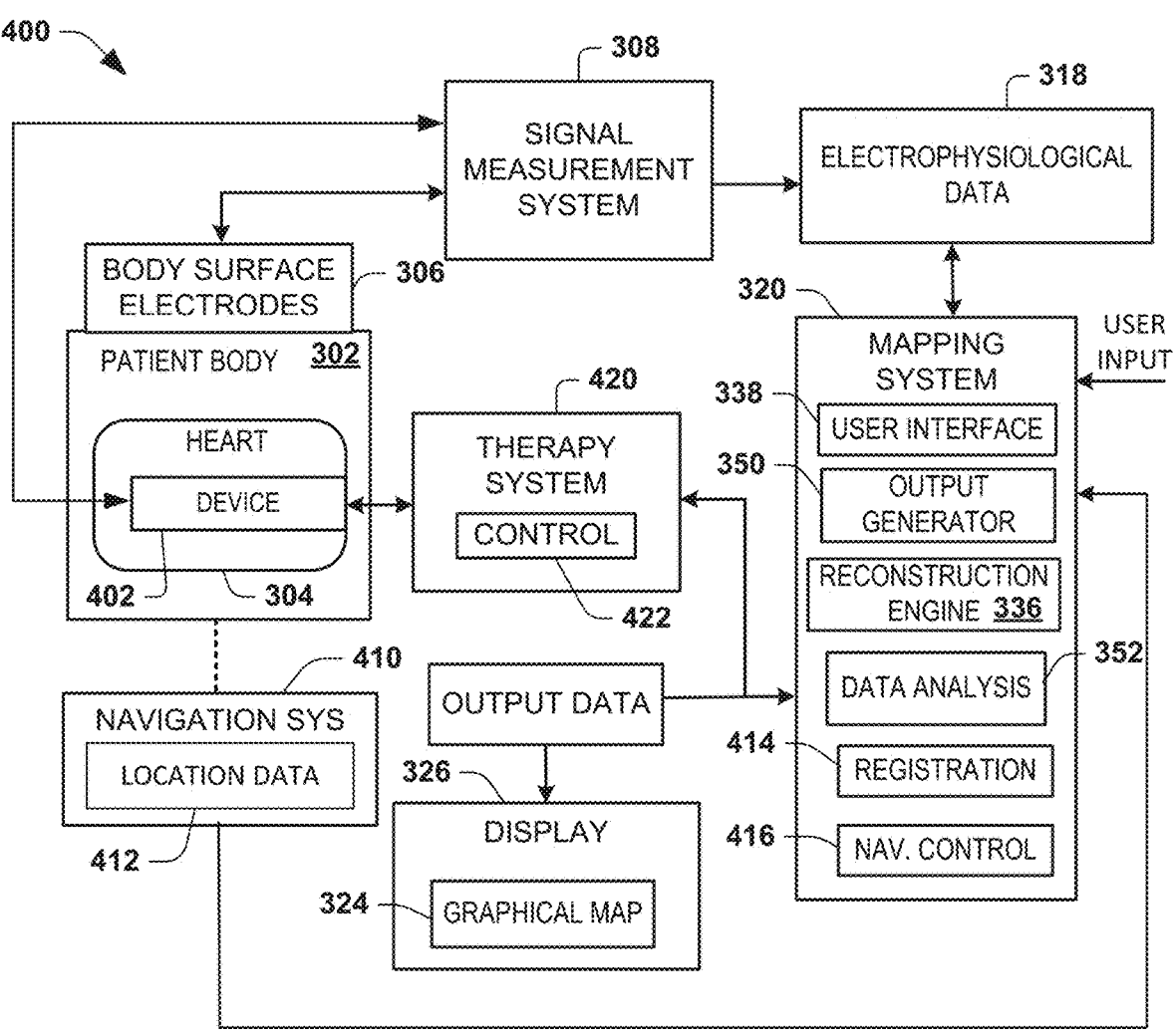
FIG. 4 is a block diagram that illustrates another example system that integrates both non-invasive and invasive functionality.

FIG. 4 is a block diagram that illustrates another example system 400 that integrates both non-invasive and invasive functionality, such as for applying a therapy based on one or more maps that can be generated. The system 400 can implement various hardware and software components shown in FIG. 3. Accordingly, the description of FIG. 4 also refers to FIG. 3. FIG. 4 focuses on additional features relating to the invasive functions and features that can be implemented, and the reader can refer back to the description of FIG. 3, as appropriate.

The system 400 includes an invasive device 402 and body surface electrodes 306. The invasive device 402 can include one or more invasive electrodes, and each of the electrodes 306 and those on the device 402 can be coupled to a signal measurement system 308 through a respective communications medium to communicate electrophysiological signals measured from the patient's body. The measurement system 308 can include an electrode interface 310 and measure unipolar, bipolar or a combination of unipolar and bipolar electrophysiological signals. Additionally or alternatively, the invasive device 402 can be implemented as or including an ablation device, such as an RF ablation probe, a cyroablation device, an irreversible electroporation (IRE) device, a laser ablation device or the like. For example, the invasive device 402 can be a catheter that is moveable within the patient's body 302, such that the position of the probe and associated electrode(s) or ablation elements can vary within the patient's body.

In FIG. 4, the system 400 also includes a navigation system 410 configured to localize the spatial position of the invasive device 402. The spatial position of the invasive device 402 can be stored in memory as location data 412. The location data 412 thus represents a three-dimensional spatial position (e.g., spatial coordinates) of the invasive device 402. The spatial location of the invasive device 402 can be with respect to the patient's body or a coordinate system of the navigation system 410. The location data 412 can also include a timestamp so that the mapping system 320 can programmatically link (e.g., synchronize) a given time instance of the geometry data, which includes location of the device 402.

As described below, for example, a spatial registration function 414 is programmed to register the spatial location of the invasive device 402, which is described by or derived from the location data 412, with respect to anatomical geometry of the patient's body 302. The registration can be repeated continually (e.g., based on a localization sample rate) or in response to detecting changes in the location data as the electrode is moved within the patient's body. In some examples, the navigation system 410 can also generate the location data 412 to include the location of one or more of the body surface electrodes 306, which are distributed across an outer surface of the patient's body (e.g., on the thorax). The location data 412 describing the location of one or more of the body surface electrodes 306 can be used to provide part of the geometry data.

Useful examples of the navigation system 410, which can be used to localize the invasive device, include the CARTO EP navigation system (commercially available from Bio-sense-Webster), the ENSITE visualization and navigation technology (commercially available from Abbott), and AcQMap (commercially available from Acutus); although other navigations systems could be used to provide the navigation data representative of the spatial position for the invasive device 402 and associated probe.

The mapping system 320 includes reconstruction engine 336, user interface 338, output generator 350 and data analysis functions 352. In the example of FIG. 4, the mapping system 320 also includes a spatial registration function 414 and a navigation control function 416. As described herein, the data analysis functions 352 can include instructions (e.g., functions 354, 356, 358 and 360 of FIG. 3) programmed to compute dominant frequency for respective baseline and modulation data sets, determine baseline dominant frequency stability based on the baseline data sets and compute an indication of dominant frequency stability (e.g., DFSI map) based on the baseline dominant stability and the dominant frequency for the modulation data set.

In the example of FIG. 4, the mapping system 320 also includes a spatial registration function (e.g., machine-readable instructions) 414 programmed to co-register the electrode geometry data and the anatomical geometry data in a common coordinate system. The spatial registration function 414 can implement one or more transforms to align spatially respective data sets for location of the invasive device 402, the location of the body surface electrodes 306 as well as the geometry for the surface of interest.

The mapping system 320 can also include a navigation control 416 programmed to provide location information (e.g., spatial coordinates on the surface of interest) so the navigation system 410 can provide further guidance to help a user move the device 402 to a target site, such as an ablation target. Electrophysiological data 318 can be recorded by the electrodes 306 (and by sensor electrodes of the invasive device) at each location within the ROI. The reconstruction engine 336 can reconstruct electrophysiological signals across the surface of interest based on the electrophysiological data recorded at each site for one or more time intervals, including baseline and modulation data sets, as described herein, and post treatment sites (e.g., for post-ablation evaluation).

As described herein, the output generator 350 configured to generate output data 322 to render one or more graphical maps (e.g., a map on a heart model) 324 and/or display processed electrical signals on the display 326 derived from the reconstructed electrical signals. The mapping system 320 can also provide information in other display formats to provide guidance to the user representative of and/or derived from electrical activity that may be measured by any combination of the electrodes 306 and electrode carried by the device 402. In the context of delivering therapy and/or measuring electrophysiological signals using an invasive device 402, the output generator 350 can provide guidance, such as a graphical, color coded representation of a DFSI map 324 on the display 326. The DFSI map 324 can thus localize one or more ablation targets (e.g., one or more spatial regions or points) on the patient's heart 304, such as by graphically differentiating the targets on the surface of interest. In an example, the ablation targets identified in the DFSI map can be supplied as output data 322 for rendering as graphical map 324 to provide guidance for targets, such as for persistent AF ablation. In another example, the DFSI map can be colocalized with targets identified in another map, which can be generated by the data analysis functions 352, such as a rotor (or rotational domain) map. The data analysis functions 352 and/or the output generator 350 can be programmed to combine the rotor map with the DFSI map and provide a resulting composite map. The composite map can be provided as output data 322 for graphical rendering on the display 326. The composite map thus can identify a subset of targets for treatment based on a correlation between the respective maps.

In a further example, the output generator 350 can generate the output data to provide guidance by instructing a user to place the invasive device 402 at one or more prescribed locations (e.g., identified targets) within the patient's body in response to output data 322. The localization of the prescribed location to the user can further be guided based on the location data 412 generated by the navigation system 410, such as in response to instructions provided by navigation control 416. For example, the navigation control 416 can be programmed to cause the spatial registration function 414 to update the geometry data 330 in response to detecting that the invasive device 402 is at or near the target location within the patient's body. For example, the navigation control function 416 is programmed to compute a distance between a position of the invasive device 402, which has been spatially registered (by spatial registration function 414) with patient anatomy (provided in geometry data), and the target location. The distance can be computed by a number of pixels along a line connecting the electrode and the prescribed location, which can be translated to a physical distance. Alternatively, the navigation system 410 can be programmed to track the distance between the electrode and the target location(s).

The reconstruction engine 336 can then reconstruct the electrophysiological signals on a surface of interest based on the updated geometry data and the electrophysiological data 318, including the electrophysiological signals measured on the outer surface of the patient's body. In some examples, the reconstruction engine 336 can reconstruct the electrophysiological signals based on the electrophysiological data 318 measured from both electrodes 306 and 402. The electrophysiological data 318 that is measured following delivery of a therapy (e.g., ablation) can also be used to validate the efficacy of the delivered therapy. For example, post-treatment electrophysiological signals can be measured by one or both electrodes 306 and 402 for one or more time intervals. In an example, at least one of the time intervals can include modulating an arrhythmia or arrhythmogenic activity, such as by administering an agent (e.g., adenosine) to the patient's body 302. The reconstruction engine 336 can provide post-treatment reconstructed electrophysiological data on the surface of interest. The data analysis functions 352 can be applied to generate one or more maps, which can be evaluated to determine whether one or more arrhythmia indicators have been reduced or eliminated.

The systems and methods of FIGS. 1-4 will be better appreciated with references to FIGS. 5A-13.

FIGS. 5A and 5B are examples of dominant frequency maps 502 and 504 showing dominant frequency determined (e.g., by DF calculator 356) during AF for respective baseline data sets. The view in the maps 502 and 506 show the dominant frequency across the heart, including the left atrium 506 and the right atrium 508. As shown by the scale 510, the DF values range between about 5 Hz and 6.5 Hz. FIGS. 5A and 5B demonstrates that in some atrial areas the DFs remain stable with time (e.g., darker colors near left atrium 506).

FIG. 6 illustrates an example stability map 600, which can be determined by DF stability calculator 358. For example, the map 600 depicts point-by-point differences between the DF maps 502 and 504 (e.g., $|\Delta DF|$) across the left and right atria 602 and 604. In this example, the point-by-point $\Delta DF$ values in the map 600 vary between zero and up to about 1 Hz with an overall absence of within-patient correlation (Pearson 0.36±0.2; p=0.29±0.13).

FIGS. 7A and 7B are DF graphical maps 702 and 704 that illustrate DF computed across the atria (e.g., by DF calculator 356) for a baseline data set. The map 702 depicts an anterior view and the map of FIG. 7B depicts a posterior view. As shown by the scale, the DF across the atria were mostly between 6 and 7 Hz.

FIGS. 8A and 8B are DF graphical maps 802 and 804 that illustrate DF computed across the atria (e.g., by DF calculator 356) for a modulation data set (e.g., during peak adenosine effect) for the same representative patient as FIGS. 7A and 7B. The maps 802 and 804 thus show the effect of adenosine on DFs in a representative patient, in which atrial regions 806 and 808 notably accelerated to be activated at DFs above 7 Hz, with steep gradients being formed in surrounding areas.

Figure 9A:
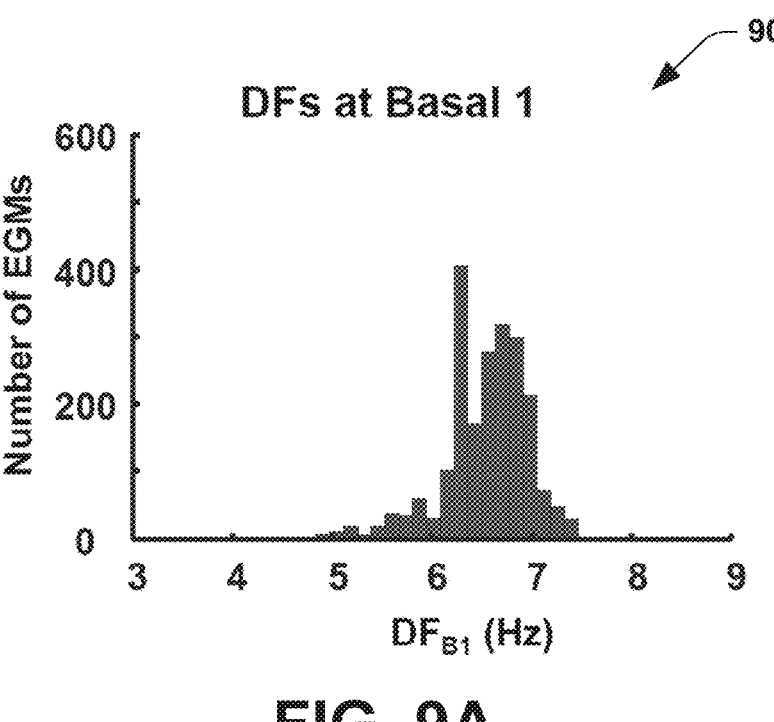
FIGS. 9A and 9B are histogram plots for baseline and modulation data sets, respectively.
Figure 9B:
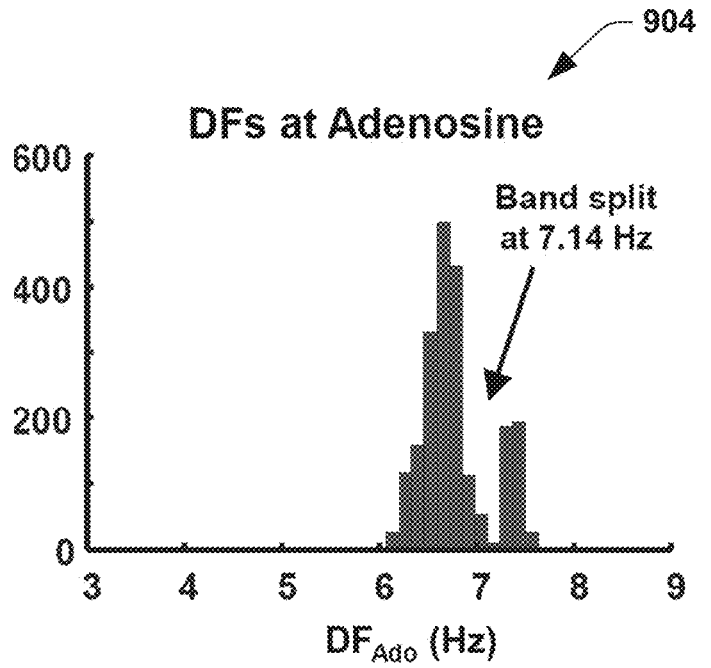

FIGS. 9A and 9B are histogram plots 902 and 904 of DFs. The plot 902 is a histogram plot for the baseline data sets of FIGS. 7A and 7B, and the plot 904 is a histogram plot for the modulation data set of FIGS. 8A and 8B. A comparison of the plots 902 and 904 illustrates a transformation in the DF distribution following the adenosine infusion. Additionally, the increased spatial DF gradient in the maps baseline plot 902 to the modulation plot 904 also manifests a re-distribution of DFs from a single mode (FIG. 9A) to a double mode (FIG. 9B), with a visible band split at about 7.14 Hz separating the single band into low and high frequency bands during adenosine infusion.

Figures 10, 11, 12:
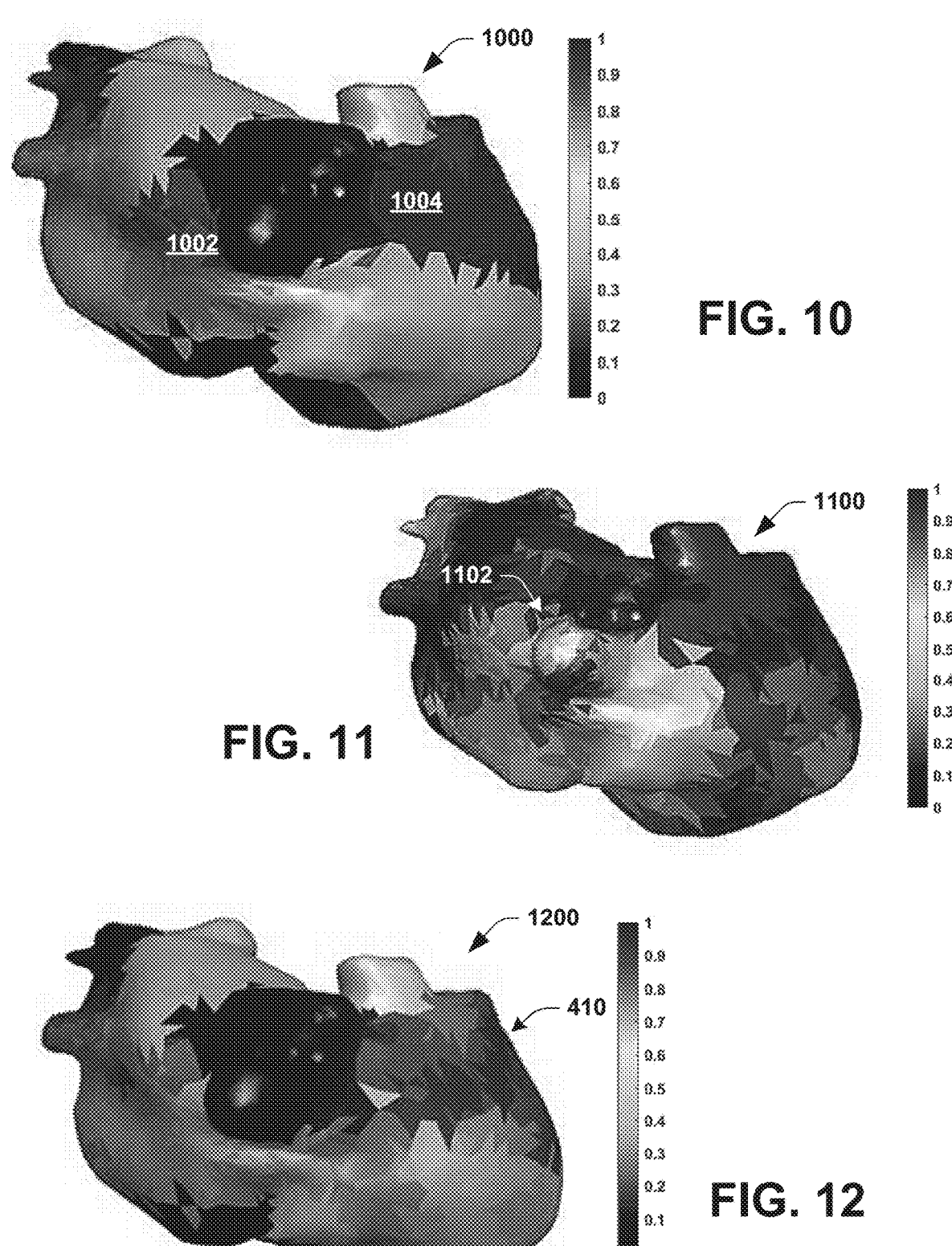
FIG. 10 is a graphical map that illustrates an example of normalized dominant frequency for a modulation data set.
FIG. 11 is a graphical map that illustrates an example of baseline normalized stability for baseline data sets.
FIG. 12 is a graphical map that illustrates an example of an index of stability across the heart.

FIGS. 10, 11 and 12 are graphical maps that illustrate respective electroanatomic maps, such as can be generated based on maps determined (e.g., by data analysis functions 356, 358 and 360) based on EP signal measurements for a given patient. FIG. 10 is a map 1000 of DF computed across the atria (e.g., by DF calculator 356) for a modulation data set (e.g., during peak adenosine effect). Similar maps not shown can be provided for respective baseline data sets. The map 1000 represents a normalized DF map for the modulation data set. As shown in FIG. 10, there were sites with higher DF levels in posterior left atrium, shown at 1002, and in the lateral right atrium, shown at 1004, with FIG. 11 is a baseline DF stability map 1100 that illustrates baseline DF stability for the given patient that can be determined (e.g., by DF stability calculator 358) based on a point-to-point difference between DF maps for first and second baseline data sets. For example, the stability map 1100 depicts a normalized indication of stability, such as can be quantified as $1-|\Delta DF|_{normalized}$ (e.g., where most stable is 1 and least stable is zero). The stability map 1100 includes a maximal baseline stability region, shown at 1102, which is co-localized with the higher DF level in the right atrium 1002 shown in FIG. 10.

FIG. 12 is an example of a stability index map 1200 that illustrates an index of stability across the atria for the given patient. The map 1200 that can be determined (e.g., by index calculator 360) based on the DF map 1000 for the modulation data set and the baseline stability map 1100. For example, the map 1200 is determined by weighting the local DF map 1000 by stability, which can be calculated as the product of the normalized DF map 1000 and normalized stability map 1100. As shown in the example of FIG. 12 the maximal and most stable DF location is at the lateral right atrial region, shown at 1202.

Figure 13:
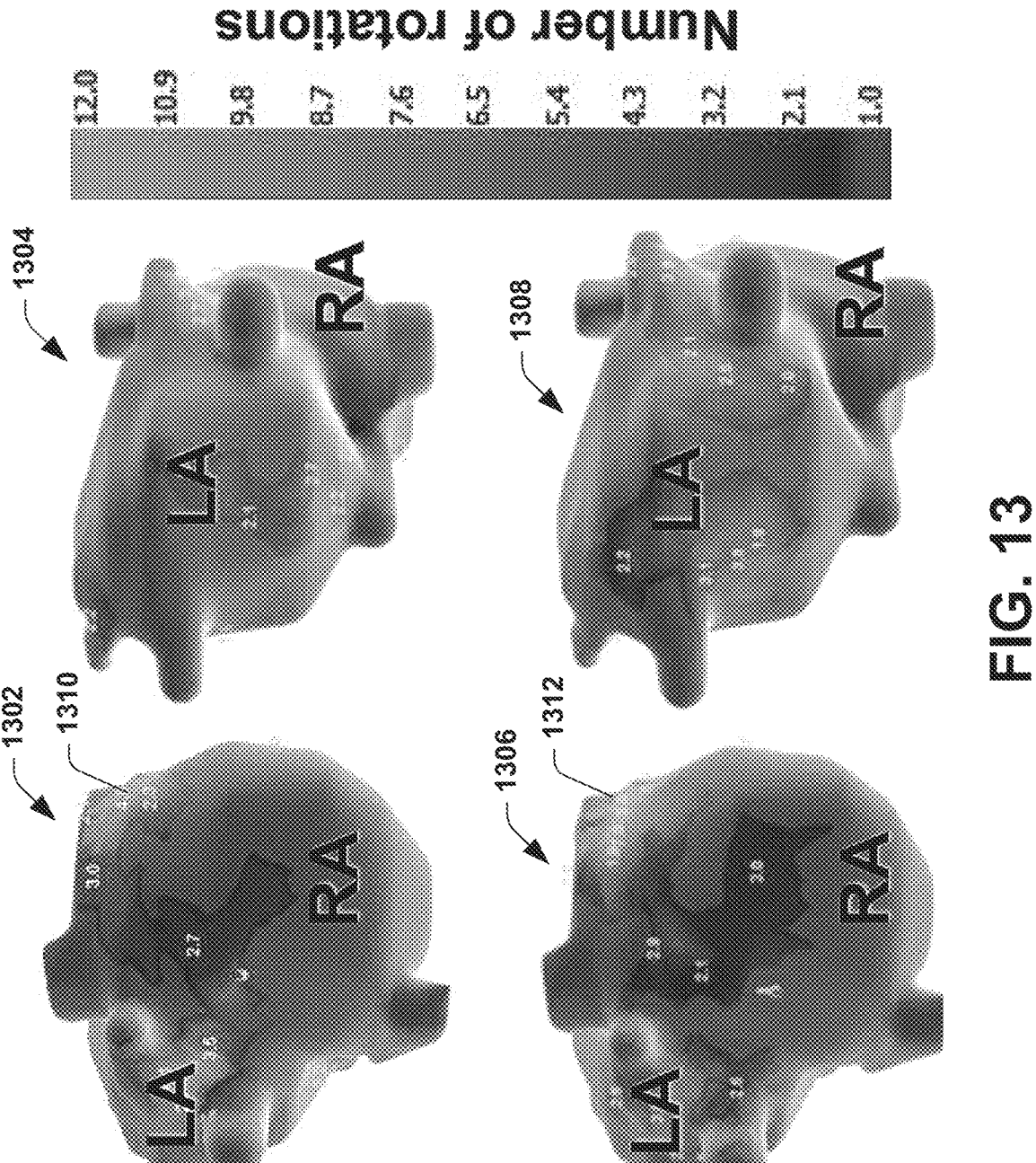
FIG. 13 are graphical maps that illustrate examples of rotational domain maps.

FIG. 13 is a set of maps 1300 that illustrate rotational domain maps for the same representative patient used to generate the maps shown in FIGS. 10, 11 and 12. FIG. 13 includes a set of rotor maps 1302 and 1304 for a first baseline data set and another set of maps 1306 and 1308 for a second baseline data set. The rotor maps can be generated by data analysis function, as described herein. The maps 1302 and 1306 demonstrate that the region 1310, 1312 with stable high rotational activity during Basal 1 and Basal 2 mappings (arrows) was also at the lateral RA, which is in correlation with the region of highest DFSI shown in FIG. 12.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

17

18

What is claimed is:

1. A method, comprising:

storing, in one or more non-transitory machine-readable media, electrophysiological data sets for multiple time intervals, at least one modulation data set including electrophysiological signals measured concurrently with modulating behavior of an arrhythmia or arrhythmogenic activity;

reconstructing, by a processor, electrophysiological signals at locations across a surface of interest based on at least some of the electrophysiological data sets, including the at least one modulation data set;

computing, by the processor, dominant frequency maps from the electrophysiological signals reconstructed for at least two baseline data sets and the at least one modulation data set, in which the dominant frequency maps include a respective dominant frequency map for each of the at least two baseline data sets and the at least one modulation data set; and analyzing, by the processor, the dominant frequency maps for the at least two baseline data sets and the at least one modulated data set to determine an indication of dominant frequency stability across at least a portion of the surface of interest.

2. The method of claim 1, wherein the method further comprises generating a graphical representation based on the indication of dominant frequency stability.

3. The method of claim 1, wherein the surface of interest includes more than one chamber of a patient's heart.

4. The method of claim 1, wherein computing the dominant frequency maps comprises:

computing a short-time Fourier transform function to produce respective frequency domain data sets for identified segments of the electrophysiological signals reconstructed for the at least two baseline data sets and for the at least one modulation data set;

computing a power spectra for each of the respective frequency domain data sets across the surface of interest; and determining the dominant frequency maps based on the power spectra for each of the frequency domain data sets.

5. The method of claim 1, wherein the method further comprises identifying segments of interest, which are free of ventricular activity, for the electrophysiological signals reconstructed for the at least two baseline data sets and for the at least one modulation data set.

6. The method of claim 5, wherein the identified segments of interest comprise TQ intervals of a cardiac cycle, wherein the dominant frequency maps are computed for the TQ intervals.

7. The method of claim 1, wherein analyzing the dominant frequency maps comprises:

identifying segments of interest for the electrophysiological signals excluding ventricular activity;

determining an indication of baseline dominant frequency stability for the segments of interest in the electrophysiological signals reconstructed for the at least two baseline data sets; and determining the indication of dominant frequency stability for locations across the surface of interest based on (i) the respective dominant frequency map for the at least one modulation data set, and (ii) the indication of baseline dominant frequency stability.

8. The method of claim 7, wherein determining the indication of baseline dominant frequency stability comprises computing a normalized baseline dominant frequency stability map based on the electrophysiological signals reconstructed for the at least two baseline data sets, and wherein determining the indication of dominant frequency stability further comprises:

computing a normalized modulation dominant frequency map based on the respective dominant frequency map for the at least one modulation data set; and multiplying the normalized baseline dominant frequency stability map and the normalized modulation dominant frequency map to provide a dominant frequency stability index map across at least the portion of the surface of interest.

9. The method of claim 8, further comprising generating guidance for delivering a therapy or treatment based on the dominant frequency stability index map.

10. The method of claim 1, further comprising administering a therapeutic agent to modulate the behavior of the arrhythmia or arrhythmogenic activity, wherein the respective dominant frequency map for the at least one modulation data set includes TQ segments of electrophysiological signals measured during peak agent-mediated effects on cardiac electrical function.

11. One or more non-transitory computer-readable media programmed to store instructions that are executable by one or more processors to perform a method, the method comprising:

computing dominant frequency maps based on reconstructed electrophysiological signal data sets for at least two baseline time intervals and at least one modulation time interval, wherein the reconstructed electrophysiological signal data sets represent electrophysiological signals at locations across a respective surface of interest within a patient's body based on measured electrophysiological signals for respective time intervals, including the at least two baseline time intervals and the at least one modulation time interval, and the at least one modulation time interval includes or overlaps with modulating a behavior of an arrhythmia or arrhythmogenic activity; and analyzing the dominant frequency maps for the at least two baseline time intervals and at least one dominant frequency map for the at least one modulation time interval to determine an indication of dominant frequency stability across at least a portion of the surface of interest.

12. The media of claim 11, wherein computing the dominant frequency maps comprises:

computing a short-time Fourier transform function to produce respective frequency domain data sets for identified segments of the electrophysiological signals reconstructed for the at least two baseline time intervals and the at least one modulation time interval;

computing a power spectra for each of the respective frequency domain data sets across the surface of interest; and determining dominant frequency across the surface of interest based on the power spectra for each of the frequency domain data sets to provide respective dominant frequency maps.

13. The media of claim 12, wherein the method further comprises selecting the identified segments of interest, comprise TQ intervals of a cardiac cycle, for the electrophysiological signals reconstructed for the at least two baseline time intervals and for the at least one modulation time interval, and the dominant frequency maps are computed for the TQ intervals.

14. The media of claim 11, wherein analyzing the dominant frequency maps comprises:

identifying segments of interest for the electrophysiological signals that exclude ventricular activity;

determining a baseline dominant frequency stability map for the segments of interest in the electrophysiological signals reconstructed for the at least two baseline time intervals; and determining the indication of dominant frequency stability based on (i) the dominant frequency map for the at least one modulation time interval, and (ii) the baseline dominant frequency stability map.

15. The media of claim 14, wherein determining the baseline dominant frequency stability map comprises computing a normalized baseline dominant frequency stability map based on the electrophysiological signals reconstructed for the at least two baseline time intervals, and wherein determining the indication of dominant frequency stability further comprises:

computing a normalized modulation dominant frequency map based on the dominant frequency map for the at least one modulation time interval; and multiplying the normalized baseline dominant frequency stability map and the normalized modulation dominant frequency map to provide a dominant frequency stability index map across at least the portion of the surface of interest.

16. The media of claim 15, further comprising generating guidance for delivering a therapy or treatment based on the dominant frequency stability index map.

17. The media of claim 11, wherein the method further comprises reconstructing electrophysiological signals at locations across the surface of interest based on at least some of non-invasively measured electrophysiological signals and geometry data, the geometry data being representative of geometry of the surface of interest and geometry of locations where the electrophysiological signals were measured.

18. A system comprising:

a computing apparatus including non-transitory memory to store data and instructions executable by a processor thereof, the data including:

reconstructed electrophysiological data sets for at least two baseline time intervals and at least one modulation time interval, the reconstructed electrophysiological data sets being representative of electrophysiological signals reconstructed at locations across a respective surface of interest based on electrophysiological signals measured for respective time intervals, the at least one modulation time interval coinciding with modulating an arrhythmia or arrhythmogenic activity, and the instructions programmed to at least:

compute dominant frequency maps from the reconstructed electrophysiological data sets for the at least two baseline time intervals and the at least one modulation time interval; and analyze, by the processor, the dominant frequency maps for the at least two baseline time intervals and at least one dominant frequency map for the at least one modulation time interval to determine an indication of dominant frequency stability across at least a portion of the surface of interest.

19. The system of claim 18, wherein the instructions to compute the dominant frequency maps comprise further instructions to:

compute a short-time Fourier transform function to produce respective frequency domain data sets for identified segments of the reconstructed electrophysiological data sets for the at least two baseline time intervals and the at least one modulation time interval;

compute a power spectra for each of the respective frequency domain data sets across the surface of interest; and determine dominant frequency across the surface of interest based on the power spectra for each of the respective frequency domain data sets.

20. The system of claim 18, wherein the instructions are further programmed to identify TQ intervals of a cardiac cycle in the reconstructed electrophysiological data sets for the at least two baseline time intervals and the at least one modulation time interval, and the dominant frequency maps are computed for the TQ intervals.

21. The system of claim 18, wherein the instructions to analyze the dominant frequency maps comprise further instructions to:

identify segments of interest for the electrophysiological signals excluding ventricular activity;

determine a baseline dominant frequency stability map for the segments of interest in the electrophysiological signals reconstructed for the at least two baseline time intervals; and determine the indication of dominant frequency stability for locations across the surface of interest based on (i) the dominant frequency map for the at least one modulation time interval, and (ii) the baseline dominant frequency stability map.

22. The system of claim 21, wherein the instructions to determine the baseline dominant frequency stability map are further programmed to determine a normalized baseline dominant frequency stability map based on the reconstructed electrophysiological data sets for the at least two baseline time intervals, and wherein the instructions to determine the indication of dominant frequency stability are programmed to:

compute a normalized modulation dominant frequency map based on the dominant frequency map determined for the at least one modulation time interval; and multiply the normalized baseline dominant frequency stability map and the normalized modulation dominant frequency map to provide a dominant frequency stability index map across at least the portion of the surface of interest.

23. The system of claim 22, wherein the instructions are further programmed to generate a graphical map that includes guidance for delivering a therapy or treatment based on the dominant frequency stability index map.

24. The system of claim 18, wherein the modulating of the arrhythmia or arrhythmogenic activity is responsive to administering a therapeutic agent.

25. The system of claim 18, further comprising:

an arrangement of body surface electrodes adapted to measure electrophysiological signals on an outer surface of a patient's body; and a signal monitoring system having inputs to receive the measured electrophysiological signals from the body surface electrodes and to provide electrophysiological measurement data representing the electrophysiological signals measured on the outer surface of the patient's body, wherein the instructions are further programmed to reconstruct electrophysiological signals on the locations distributed across the surface of interest based on the electrophysiological measurement data and geometry data, the geometry data representing geometry of the surface of interest and locations of the respective body surface electrodes in three-dimensional space.

\* \* \* \* \*